United States Patent [19]

Sommer et al.

[11] 4,351,970

[45] Sep. 28, 1982

[54] METHOD OF PREPARING ALCOHOLS HAVING TWO TO FOUR CARBON ATOMS BY CATALYTIC HYDRATION OF OLEFINS

[75] Inventors: August Sommer; Wilhelm Heitmann, both of Herne; Rainer Brücker, Castrop-Rauxel, all of Fed. Rep. of Germany

[73] Assignee: Veba-Chemie Aktiengesellschaft, Gelsenkirchen-Buer, Fed. Rep. of Germany

[21] Appl. No.: 151,991

[22] Filed: May 21, 1980

Related U.S. Application Data

[63] Continuation of Ser. No. 973,993, Dec. 28, 1978, abandoned.

[30] Foreign Application Priority Data

Dec. 31, 1977 [DE] Fed. Rep. of Germany ....... 2759237

[51] Int. Cl.³ .............................................. C07C 29/04
[52] U.S. Cl. .................................. 568/895; 568/896; 568/898; 568/899
[58] Field of Search ............... 568/896, 899, 895, 897, 568/898, 900, 901

[56] References Cited

U.S. PATENT DOCUMENTS

| | | | |
|---|---|---|---|
| 2,050,445 | 8/1936 | Metzger | 568/896 |
| 2,648,711 | 8/1953 | Carrier | 568/896 |
| 2,960,477 | 11/1960 | Smith et al. | 568/896 |
| 3,686,334 | 8/1972 | Britton | 568/896 |
| 3,953,533 | 4/1976 | Sommer et al. | 568/896 |
| 4,087,471 | 5/1978 | Bowman et al. | 578/899 |

*Primary Examiner*—Joseph E. Evans
*Attorney, Agent, or Firm*—Sprung, Horn, Kramer & Woods

[57] ABSTRACT

A method is disclosed of preparing alcohols having 2 to 4 carbon atoms by catalytic hydration of the corresponding olefins on acid catalysts at elevated temperature and elevated pressure, characterized in that byproducts of the hydration, namely corresponding ethers and/or low-polymerized hydrocarbons and/or undesired alcohols, which form upon the passage of the input product through catalyst bed, are fed to the input product before entry into the reactor, said method being characterized in that:

A. When ethylene is the olefin, the reaction is conducted at a temperature of 200°–300° C.; and B: When propylene is the olefin the reaction is conducted at a temperature of 150° to 220° C.

14 Claims, 1 Drawing Figure

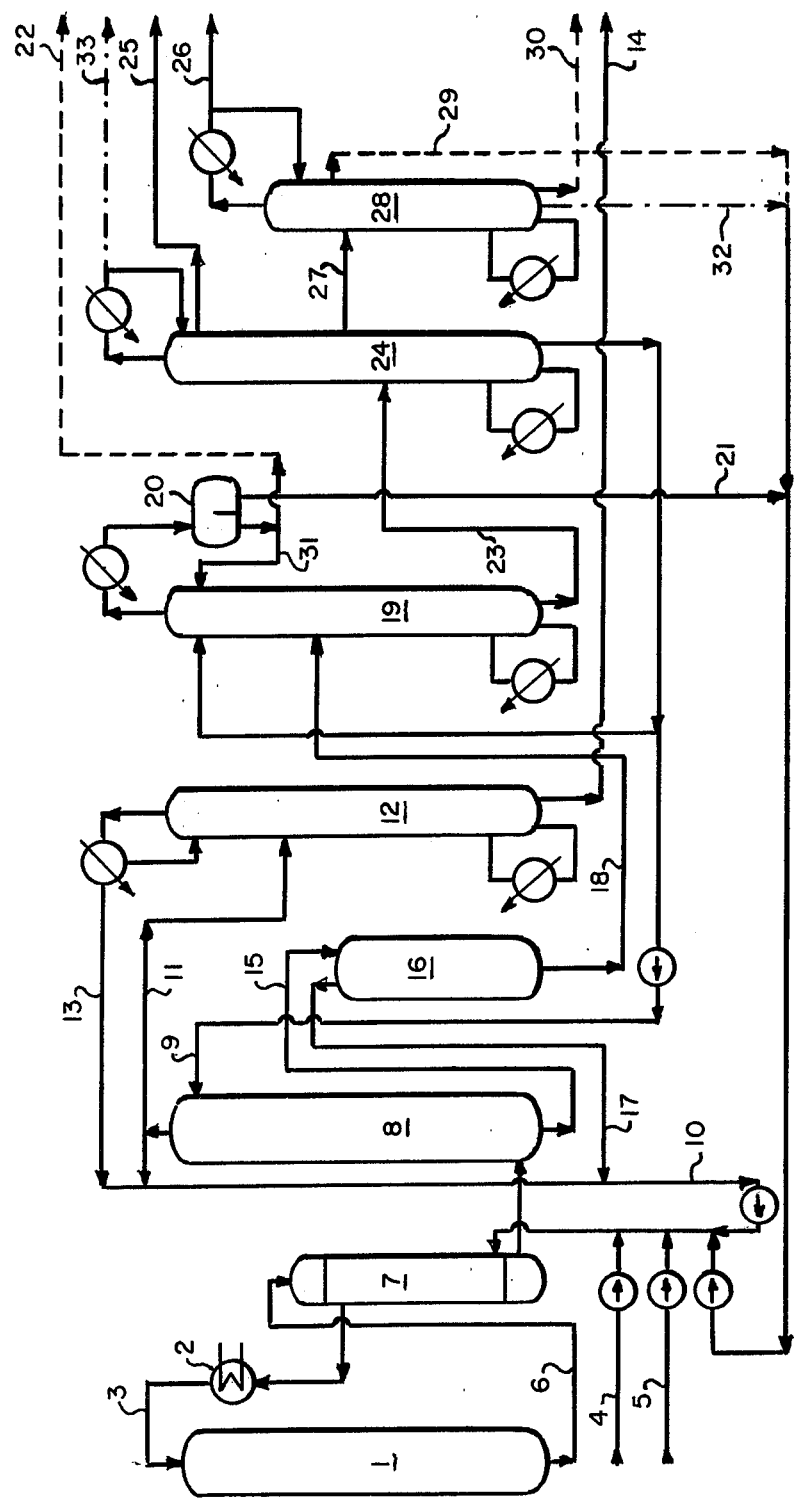

METHOD OF PREPARING ALCOHOLS HAVING TWO TO FOUR CARBON ATOMS BY CATALYTIC HYDRATION OF OLEFINS

This is a continuation of application Ser. No. 973,993 filed Dec. 28, 1978, now abandoned.

DESCRIPTION AND EXAMPLES

It is known to prepare aliphatic alcohols, especially ethyl alcohol, isopropyl alcohol, and secondary and tertiary butyl alcohol by passing olefins, that is especially ethylene, propylene or butenes, together with water over acid catalysts at elevated temperature and elevated pressure. The catalyst is principally phosphoric acid, which is adsorbed onto porous supports, or ion exchangers in the H form. It is furthermore known that, in addition to the desired reaction for the formation of alcohol, secondary reactions take place under the reaction conditions between olefins and other olefin molecules or with water or with both, which result not only in a contamination of the principal product but also in a reduction of the yield, since the by-products have to be separated from the principal product and eliminated. Such secondary products are mainly hydrocarbons which form from the combination of several olefin molecules, ethers formed from two olefin molecules reacting with a water molecule, alcohols other than desired which are either isomers of the desired alcohol or higher alcohols which form by the reaction with water of olefins which have formed first by oligomerization of the starting olefins, and finally aldehydes and ketones which form from the alcohols by dehydrogenation under the reaction conditions.

As regards quantity, the ethers predominate among the by-products, followed by hydrocarbons and undesired by-product alcohols, while the aldehydes and ketones form in the least significant amounts. Otherwise the amount of by-products that form depends largely on the reaction conditions, namely temperature, pressure, catalytic detention time and the molar ratio of water to olefin.

In principle, it is to be expected that the formation of by-products is due to chemical reaction which takes place in both directions, and the transformation that finally is accomplished depends, if the catalytic detention time is sufficiently long, on the equilibrium concentrations of the reactants under the reaction conditions and on the starting concentration. Exceptions are those by-products which certainly form irreversibly, that is, where one or more end products are no longer available for the equilibrium. This applies, for example, to oligomerization products of the olefin having such a high molecular weight that no appreciable vapor pressure is present under the reaction conditions. It also applies, however, to the formation of the aldehydes and ketones, because the hydrogen that develops in the dehydrogenation can react with the olefin that is present in great excess, with the formation of paraffin, so that it does not serve as a member of the equilibrium.

For both groups of compounds--highly polymerized hydrocarbons as well as aldehydes and ketones--it has been proven experimentally, for cases of the direct gas phase hydration of water with ethylene or propylene to ethyl alcohol or isopropyl alcohol, that they do not form as products of an equilibrium reaction. When these substances are added to the starting gas in the reactor in an amount on the order of that which forms as by-product under the reaction conditions, it has been found that the formation of by-product in this respect cannot be suppressed, and that instead the total amount of these substances that occurs is composed additively of the amount that forms ordinarily under the reaction conditions and the amount added. Losses of yield in this direction can therefore be reduced to a certain extent by an appropriate choice of the reaction conditions, but they cannot be entirely prevented. Aldehydes and ketones have a solubility in water that is similar to that of the corresponding alcohols, and thus they are removed with the product alcohols from the circulating olefin, so that no higher concentrations build up. From the alcohol that is produced, the aldehydes and ketones must, of course, be removed if the purity requirements necessitate it. The higher molecular weight hydrocarbons remain largely in the circulating olefin when the alcohol is separated, and can be separated in a rational manner, as described in German Pat. Nos. 1,768,207 and 1,960,139, by distilling a portion of the circulating olefin so as to avoid transformation losses and possible clogging of the apparatus with products of further polymerization.

On the other hand, it has long been known that the ethers corresponding to the alcohols involved form in an equilibrium reaction. Without going into the complicated theories of the formation of ethers, their formation can be explained most easily on a purely stoichiometric basis as a further reaction of the alcohol that forms with an additional olefin molecule, as for example:

$$C_2H_5OH + C_2H_4 \rightarrow (C_2H_5)_2O$$

or $C_3H_7OH + C_3H_6 \rightarrow (C_3H_7)_2O$.

All three of the reactants, i.e., alcohol, olefin and ether, are available to the equilibrium. They are not among the previously mentioned substances, i.e., highly polymerized hydrocarbons and aldehydes or ketones, which are not available to the equilibrium, because either the vapor pressure is too low, or, due to the considerable excess of one reactant, a virtually quantitative further reaction takes place.

Thus, in U.S. Pat. No. 2,050,445, in the case of the preparation of ethanol in a continuous process with aqueous phosphoric acid as catalyst, it was reported (page 3, left column, lines 44–54) that the further formation of ether can be suppressed by recycling diethyl ether with the circulation gas. The recycling of diisopropyl ether to the circulation gas of isopropyl alcohol synthesis from propylene is described in Canadian Pat. No. 867,797. And so, in the synthesis of ethanol and isopropyl alcohol, it has long been the practice in ethanol and isopropyl alcohol syntheses to recycle the corresponding ethers in the amount in which they are produced to the circulating gas for the purpose of increasing the yield.

The yield of desired alcohol, however, is further reduced by other by-products, i.e., hydrocarbons of low degree of polymerization and unwanted alcohols, which also require additional distillation for purification.

It was therefore the object of the invention to find a way to suppress the formation by these by-products, namely hydrocarbons of low polymerization and unwanted alcohols.

It has unforeseeably and surprisingly been found that also if the undesired alcohols and hydrocarbons of low polymerization which develop as by-products of the hydration are added to the input olefin, the further formation of these compounds is suppressed, and the yields of desired alcohol are thereby increased.

The subject matter of the invention is therefore a method of preparing alcohols having 2 to 4 carbon atoms by the catalytic hydration of the corresponding olefins on acid catalysts at elevated temperature and elevated pressure, characterized in that by-products of the hydration, namely corresponding ethers and/or hydrocarbons of low polymerization and/or undesired alcohols which form upon the passage of the input product through the catalyst bed are fed to the input product before it enters the reactor.

The by-products can be recycled in an amount of the order of magnitude of that in which they form, or else in amounts of 0.01 to 3 parts per part of the forming by-product.

In the case of the undesired alcohols which form as by-product, and which therefore are either isomers of the desired product or have developed by the addition of water onto oligomerization products of the starting olefin, it was quite uncertain, on the basis of the theory, whether the addition of these substances to the circulation gas would result in the desired suppression of their formation. In the case of the alcohols derived from the oligomerization products of the starting olefin, it was uncertain whether two successive, different reactions are necessary for their formation, and it appears quite doubtful whether the two back-reactions would take place under the existing reaction conditions with the speed that would be necessary in order to be able to be certain that these compounds will no longer develop.

It was still more improbable, however, that in the case of the compounds isomeric with the desired alcohol, it might be possible to suppress their formation by adding them to the input olefin. These isomers, such as n-propanol and n-butanol, for example, develop in small amounts contrary to Markownikow's law according to which isopropyl alcohol and secondary butanol would have to develop. Only in the case of hydration in accordance with Markownikow's law is it possible to imagine a mechanism for a reaction catalyzed by protons, for example:

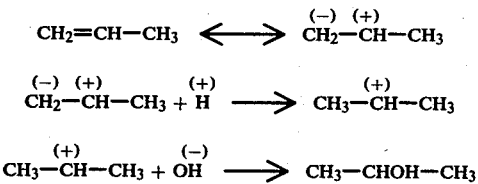

In other words, first the proton reacts with the carbeniate carbon atom which is present in the polar boundary structure of the olefin. In this comprehensible reaction, reversal in the presence of acid is plausible, so that there is no doubt that an equilibrium reaction is involved, which is not true of the isomers which develop contrary to Markownikow's law.

In the case of the low molecular weight hydrocarbons as products of a small number of oligomerization stages, it is theoretically more likely that an equilibrium reaction is involved, say:

$$C_2H_4 + C_2H_4 \rightarrow C_4H_8, \quad C_4H_8 + C_2H_4 \rightarrow C_6H_{12}$$

$$C_3H_6 + C_3H_6 \rightarrow C_6H_{12}, \quad C_6H_{12} + C_3H_6 \rightarrow C_9H_{18}.$$

Since these low molecular weight hydrocarbons behave in the distillation in the presence of water vapor like the ethers, they can be recycled simply by omitting the refining of the raw ether separated from the raw alcohol by hydroselective distillation prior to recycling it to the input olefin. At the same time, by following the procedure of circulation gas cleaning described in German Pat. Nos. 1,768,207 and 1,960,139, care must be taken to see to it that any hydrocarbons of higher molecular weight that might be recycled with the circulation gas are purged out and the low molecular weight hydrocarbons are left in.

The compounds which are to be recycled are the corresponding ethers, low molecular weight hydrocarbons from the oligomerization of the starting olefin, and all alcohols forming as by-product, including isomers of the desired main product and hydration products of the oligomers of the starting olefin. Since it is assumed that all of the named compounds are formed in equilibrium reactions, the amount added to the circulation gas need only be of the same order of magnitude as the amount produced under the reaction conditions. Especially when the reaction conditions change, the amount that develops is not precisely known until the by-products occur in the distillation. If slightly greater amounts of the by-products are added than corresponds to the momentary formation, the equilibrium concentration will be established also for all of the named substances, and then, balance-wise, by-product is converted back to olefin or to olefin and water.

It is possible either to feed back into the circulation gas all of the named by-products simultaneously in an amount corresponding to the order of magnitude of their formation, or to eliminate some of them and feed back only the others. This is important especially when some of the by-products are otherwise economically valuable, as is often the case with diethyl ether, for example.

In addition to an increase of the olefin's yield of the desired alcohol, the invention also greatly simplifies the rectification of the raw alcohol that is produced. For example, the rectification of the ether produced as the top layer of the product from the hydroselector is eliminated; also, the side stream from the alcohol rectifier, which contains the by-product alcohols, does not have to be freed either of the main product alcohol contained in it or of water, when it is reused in the hydration, since water is put in anyway as raw material, and small amounts of recycled main product do slightly reduce the transformation, but do not as adversely effect the economically more important yield as would discarding it.

The reaction conditions in the hydration of the olefins range as follows:
Hydration in the gaseous phase:
Ethanol:200°–300° C., 30–100 bars
    Water-to-olefin ratio 0.2:1 to 1:1
Isopropanol:150°–220° C., 10–50 bars
    Water-to-olefin ratio 0.2:1 to 0.8:1
Butanols:150°–220° C., 10–50 bars
    Water-to-olefin ratio 0.2:1 to 1.2:1;
Hydration in the liquid phase and mixed phase:
Isopropanol:120°–160° C., 30–200 bars
    Water-to-olefin ratio 1:1 to 30:1

Butanols: 100°–150° C., 20–100 bars
Water-to-olefin ratio 1:1 to 30:1

The invention will be explained by the following examples in conjunction with the appended drawing.

EXAMPLE 1

In an apparatus for the production of ethanol by the hydration of ethylene, which consists of a reactor 1 filled with 18 cubic meters of a siliceous support having an $H_3PO_4$ content of 38 weight-percent, to which 25,470 kilograms of ethylene and 5,420 kg of water are fed hourly through line 3 at a synthesis pressure of 70 bars and a synthesis temperature of 235° C. which is established in a preheater 2, so that a water-to-olefin molar ratio of 0.3:1 prevails, 1,050 kg of ethylene is transformed hourly to 1,695 kg of ethanol, the yield thus being 98% and the transformation of the input ethylene 4.2%. The reacted ethylene is replaced by fresh gas from line 4, and the process water is fed in through line 5. The high yield is achieved by the recycling of much of the by-products:

After the gas mixture leaving the reactor 1 through line 6 has been cooled in heat exchanger 7 countercurrently to the cold circulation gas and has been washed in washer 8 with water from line 9, all of the water-soluble reaction products have been removed from the unreacted ethylene, and it is recycled through line 10 by a circulation compressor to the reactor 1 together with fresh ethylene, process water and the recycled by-products.

For the removal from the circulation gas of the by-products which are not soluble in water, these being largely more highly polymerized hydrocarbons, a portion of the circulation gas is fed through line 11 to the ethylene purification column 12. Purified ethylene passes through the top of this column through line 13 to the circulation gas, and high-boiling impurities are purged out of the sump through line 14. At the production figures given, these amount to only 17 kilograms, corresponding to a loss of yield of 1.6%.

The dilute raw alcohol from the washer 8 passes through line 15 to the expansion tank 16; the dissolved gas that is liberated by the expansion passes through line 17, and a compressor that is not shown, to the circulation gas. The expanded raw alcohol is fed through line 18 to the hydroselection column 19 in which the steam-volatile impurities of the alcohol, i.e., diethyl ether, low-boiling hydrocarbons and acetaldehyde, are separated by feeding wash water to the top. The product taken from the top separates in the decanter 20 into an aqueous layer and an organic layer. The organic layer amounts to about 46 kg having the following composition: 2.6% hydrocarbons, 93.0% diethylether, 1.2% acetaldehyde, 0.6% ethanol, 1.8% butanols, and 0.8% water, and is recycled through line 21 to the circulation gas; the aqueous layer contains most of the acetaldehyde and amounts to 176 kg containing 5.3% diethylether, 3.0% acetaldehyde, 0.6% ethanol, 0.1% butanols, and 91.0% water, and is withdrawn to purge out the acetaldehyde through line 22. In a column which is not represented, acetaldehyde is separated through the top as an azeotrope with ether (7 kg containing 76.0% acetaldehyde and 24.0% diethyl ether). With respect to alcohol, this is a yield loss of 0.4%. The sump product is fed, like the organic layer of the decanter, to the circulation gas.

The dilute, partially purified alcohol passes from the hydroselection column 19 through line 23 to the rectifying column 24 where ethanol boiling azeotropically with water is withdrawn from the top as product and is carried off through line 25, while the pure water obtained as the sump product is used as wash water.

In the center of the rectification column the higher boiling alcohols concentrate, which have formed as by-products, because they have a higher boiling point than ethanol, but differ from it only slightly in steam volatility depending on their concentration. They are fed through line 27 to a side column 28 in which they are further concentrated and are recycled to the circulation gas through line 29 at about 12 kg/h, with the following composition: 40.2% ethanol, 38.0% butanols, 21.8% water. The head product is combined through line 26 with the product from line 25; both streams can be absolutized for the complete removal of water. In the sump of the side column, water is removed through line 30. When the side column 28 is operated in the described manner, no by-products are purged out to reduce the yield.

EXAMPLE 2

In an apparatus for the production of isopropyl alcohol by the hydration of propylene, which consists of a reactor 1 filled with 20.5 cubic meters of siliceous support and having an $H_3PO_4$ content of 25 wt.-%, to which 65,000 kilograms of propylene plus 7,500 kg of water are fed hourly at a synthesis pressure of 40 bars and a synthesis temperature of 180° C. which is established in the preheater 2, so that the molar ratio of water to olefin is 0.3:1, 2,644 kg of propylene is reacted hourly to form 3,690 kg of isopropyl alcohol, that is, the yield is 98%, and the transformation of the input propylene amounts to 4.1%. The transformed propylene is replaced with fresh propylene from line 4 and the process water is fed in through line 5. The high yield is achieved by substantial recycling of the by-products, in the following manner:

After the gas mixture leaving the reactor 1 through line 6 has been cooled countercurrently by the cold circulation gas and has been washed in washer 8 with water from line 9, all of the water-soluble reaction products have been removed from the unreacted propylene, and it is recycled through line 10 by the circulation gas compressor to the reactor 1 together with fresh propylene, process water and the recycled by-products.

For the removal from the circulation gas of the non-water-soluble by-products, which are essentially hydrocarbons of a higher degree of polymerization, a portion of the circulation gas is fed through line 11 to the propylene purification column 12. Purified propylene passes from the top of this column through line 13 back to the circulation gas and high-boiling impurities are purged from the sump through line 14. The production figures given, however, amount to only 47 kg, which corresponds to a loss of yield of 1.6%.

The diluted raw alcohol from the washer 8 passes through line 15 to the expansion tank 16; the gas that is released by the expansion passes through line 17 and a compressor which is not shown, back to the circulation gas. The raw alcohol from the expansion passes through line 18 to the hydroselection column (19) in which the steam-volatile impurities of the alcohol, i.e., diisopropyl ether and low-boiling hydrocarbons, are separated through the top by the injection of washing water. The head product separates in the decanter 20 into an aqueous layer and an organic layer. The organic layer has approximately the following composition: 16.5% hydrocarbons, 81.1% diisopropyl ether, 0.1% acetone, 0.1% isopropyl alcohol, 2.2% hexanols; it is returned through line 21 to the circulation gas. The aqueous layer has approximately the following composition: 2.1% diisopropyl ether, 0.1% hexanols, 0.1% acetone, 0.3% isopropyl alcohol, 97.4% water, and it is returned as reflux to the hydroselection column 19 through line 31. The dilute, partially purified alcohol runs from the hydroselection column 19 through line 23 to the rectification column 24 where isopropyl alcohol boiling azeotropically with water is obtained as product near the top and is drawn off through line 25, while the pure water sump product is used as wash water.

Acetone concentrates in the top of the rectification column 24, and therefore a portion of the reflux is withdrawn through line 33 and distilled in a column which is not represented. The sump product of this column is returned to the reflux from the rectification column, while acetone is purged out at the top. At the production figures given, approximately 6 kg of top product is obtained per hour, having the following composition: 75% acetone, 15% isopropyl alcohol, 10% water; this corresponds to a yield loss of 0.2%.

In the middle of the rectification column 24 the higher boiling alcohols (principally n-propanol and hexanols) concentrate, which have formed as by-products. Like acetone, they differ only slightly from the isopropyl alcohol in steam volatility. They are fed through line 27 to a side column 28 in which they are collected together with the water as sump product and are returned to the circulation gas through line 32. Their composition is approximately 0.9% isopropyl alcohol, 2% hexanols, 4% n-propanol and 93.1% water. The product from the top of the side column 28 is combined through line 26 with the production from line 25; for complete freedom from water, both streams can also be treated with dehydrating agents. When the side column 28 is operated in the manner described, no by-products are purged from it to reduce the yield.

EXAMPLE 3

In an apparatus for the production of ethanol by the hydration of ethylene in the manner and under the conditions described in Example 1, the product in line 29 is fed with 10 kg/h of a butanol mixture of the following composition: 79 wt.-% butanol, 6% n-butanol, 4% isobutanol, 1% tert.-butanol, and 10% water, and is added to the circulation gas of the synthesis as described in Example 1. It is apparent that then the amount of butanols in the product in line 18 has not increased above the amount of butanol that was here before the addition of butanol mixture to the stream in 29.

EXAMPLE 4

In an apparatus for the production of sec.-butanol by the hydration of a mixture of butene-(1) and butene-(2) with steam on a catalyst of $H_3PO_4$ applied to a siliceous support, in a concentration of 20 wt.-% at a temperature of 195° C. at the reactor input, a pressure of 20 bars, and a molar ratio of butene to water of 1:1.05, the procedure being otherwise analogous to Examples 1 and 2, the non-water-soluble top product from the hydroselection which is produced in line 21 during the distillation, and which consists substantially of sec.-butyl ether and the alcohol and water mixture in line 29, containing sec.-butanol, isobutanol, n-butanol and octanols, is fed to the circulation gas. The yield of secondary butanol is thus increased from 89.5 to 96.2%.

EXAMPLE 5

In an apparatus for the preparation of isopropyl alcohol by the hydration of propylene with water on heterogeneous phase on a highly acid cation exchange resin in the $H^+$ form, the reactor 1 is in the form of a tube reactor having interposed distributor trays. The individual tube clusters have a length of 4 meters, and the tubes have an inside diameter of 40 mm. The temperature at the input is 135° C., the pressure 70 bars, and the molar ratio of water to propylene is 8:1. An LHSV (liquid hourly space velocity) of 1.4 m/h is selected as the rate of input. The ion exchanger is a sulfonated copolymer of styrene and p-divinylbenzene of the macroreticular type (Lewatit SP 120 of Bayer AG).

The reaction mixture leaving the reactor 1 through line 6 is cooled in the heat exchanger 7 countercurrently to the input product, and then additionally cooled with water down to 90° C.; the organic phase is freed of isopropyl alcohol in the extractor 8 countercurrently with five times the volume of water fed in through line 9, and it is wholly or partially recycled through line 10 to the reactor. The aqueous phases are fed through line 15 to the expander 16, and then further treated as described in Example 2.

The yield of isopropanol amounts to 99.5% with respect to the reacted propylene. This high yield is achieved by recycling to the reactor through line 13 the by-products, which are essentially diisopropyl ether and oligomers of propylene, and recycling to the reactor through line 32 the undesired alcohols such as 4-methylpentanol-(2), 2-methylpentanol-(2), n-propanol, and, to a lesser extent, nonanols.

We claim:

1. Method of preparing alcohols having 2 or 3 carbon atoms by catalytic hydration of the corresponding olefins on acid catalysts at elevated temperatures and elevated pressure, characterized in that by-products of the hydration including organic soluble by-products which include low-polymerized hydrocarbons which form upon the passage of the input product through the catalyst bed, are separated from the alcohol product and fed to the input product before entry into the reactor, said method being characterized in that:
   A. if ethylene is the olefin, the reaction is conducted at a temperature of 200°–300° C. in the gas phase;
   B. if propylene is the olefin the reaction is conducted at a temperature of 150° to 220° C. in the gas phase or 120° to 160° C. in the liquid or mixed phase.

2. Method of claim 1, characterized in that the by-products of the hydration are fed to the input product before entry into the reactor, in an amount corresponding to the order of magnitude in which they form during the passage of the input product through the catalyst bed.

3. Method of claim 1, characterized in that the by-products of the reaction are fed to the input product before entry into the reactor, in amounts of 0.01–3 parts per part of the developing by-product.

4. Method of claim 1 wherein ethylene is the olefin and diethyl ethers, oligomers of ethylene, butanols and hexanols are recycled.

5. Method of claim 1 wherein the olefin is propylene and diisopropyl ether, oligomers of propylene, n-propanol, hexanols, methylpentanols and nonanols are recycled.

6. A process for preparing alcohols having 2 to 4 carbon atoms by catalytic hydration of the corresponding olefins on acid catalysts at elevated temperatures and elevated pressures, characterized in that byproducts of the hydration including organic soluble byproducts which include low polymerized hydrocarbons which form upon the passage of the input product through the catalyst bed, are fed to the input product before entry into the reactor, said method being characterized in that:

A. if ethylene is the olefin, the reaction is conducted at a temperature of 200°-300° C. in the gas phase;
B. if propylene is the olefin, the reaction is conducted at a temperature of 150° to 220° C. in the gas phase or 120° to 160° C. in the liquid or mixed phase; and
C. if the olefin is a butene, the reaction is conducted at 150°-220° C. in the gas phase, or 100°-150° C. in the liquid or mixed phase, said process being further characterized in that the alcohol is separated from the byproducts and byproducts comprising a mixture of ethers, low-polymerized hydrocarbons and undesired alcohols are recycled, following separation of the alcohol to the reactor.

7. A process according to claim 6, wherein the alcohols are formed in a gas phase reaction.

8. A process according to claim 7, wherein ethylene is the olefin, the reaction is conducted in the gas phase at 200° to 300° C. under a pressure of 30 to 100 bars.

9. A process according to claim 7, wherein propylene is the olefin, the reaction is conducted in the gas phase at a temperature of 150° to 220° C. under a pressure of 10 to 50 bars.

10. A process for preparing a butanol by catalytic hydration of a butene on an acid catalyst at 150°-220° C. in the gas phase or 100°-150° C. in the liquid or mixed phase, characterized in that byproducts of the hydration including organic soluble byproducts which include low polymerized hydrocarbons which form upon the passage of the butene through the catalyst bed, are fed to the butene before entry into the reactor, said process being further characterized in that following separation of the butanol, impurities comprising a mixture of higher alcohols, oligomers of butene and ethers are recycled.

11. A method according to claim 1 wherein all of the by-products of the hydration including those which are water-soluble and those which are soluble in an organic solvent are fed to the input product before entry into the reactor.

12. A method according to claim 11 wherein said by-products are fed to the input product at a rate corresponding the order of magnitude of their formation.

13. A method according to claim 1 wherein the reaction product is subjected to purification which includes a rectification, higher alcohols which are formed during the process and/or the rectification in admixture with the desired alcohol are removed from the rectification column and recycled to the input product before its entry into the reactor.

14. A method for preparing alochols having 2 to 4 carbon atoms by catalytic hydration of the corresponding olefins on acid catalysts at elevated temperatures and elevated pressures, characterized in that the by-products of the hydration including organic soluble byproducts which include low polymerized hydrocarbons which form upon the passage of the input product through the catalyst bed, are fed to the input product before entry into the reactor, said method being characterized in that:

A. if ethylene is the olefin, said reaction is conducted at a temperature of 200°-300° C. in the gas phase;
B. if propylene is the olefin, the reaction is conducted at a temperature of 150° to 220° C. in the gas phase or 120° to 160° C. in the liquid or mixed phase; and
C. if the olefin is a butene, the reaction is conducted at 150°-220° C. in the gas phase or 100°-150° C. in the liquid or mixed phase, said process being further characterized in that following the hydration, the aqueous product is contacted with an organic solvent whereby there is formed an aqueous phase and an organic phase and said organic phase containing water-insoluble byproducts if fed to the input product before entry into the reactor.

* * * * *